US00PP10155P

United States Patent [19]

Twomey

[11] Patent Number: Plant 10,155

[45] Date of Patent: Dec. 23, 1997

[54] GRANDIFLORA ROSE VARIETY NAMED 'TWOFAVOR'

[75] Inventor: Jerry Twomey, Watsonville, Calif.

[73] Assignee: DeVor Nurseries, Inc., Watsonville, Calif.

[21] Appl. No.: 415,171

[22] Filed: Mar. 31, 1995

(Under 37 CFR 1.47)

[51] Int. Cl.[6] ..... A01H 5/00

[52] U.S. Cl. ..... Plt./18

[58] Field of Search ..... Plt./18, 19, 26, Plt./27

[56] References Cited

U.S. PATENT DOCUMENTS

P.P. 3,749 7/1975 Byrum ..... Plt./18
P.P. 4,057 5/1977 Jelly ..... Plt./29

*Primary Examiner*—Howard J. Locker
*Attorney, Agent, or Firm*—Christie, Parker & Hale, LLP

[57] ABSTRACT

A grandiflora rose variety producing pink flowers.

1 Drawing Sheet

SUMMARY OF THE INVENTION

The present invention relates to a new and distinct grandiflora rose variety which was originated by my crossing as seed and pollen parents, varieties named 'Emily Post' U.S. Plant Pat. No. 3,749, and 'Royalty', U.S. Plant Pat. No. 4,057, respectively. The varietal denomination of this new rose is 'Twofavor'.

Among the novel characteristics possessed by this new variety which distinguish it from its parents and all other varieties of which I am aware are its vigor and resistance to blackspot, mildew, and rust, and attractive flowers with strong musk fragrance.

Asexual reproduction by budding of the new variety as performed in Watsonville, Calif., shows that the foregoing and other distinguishing characteristics come true to form and are established and transmitted through succeeding propagations. Other known forms of asexual reproduction may be also employed.

Comparison with Parents

The seed parent, 'Emily Post', produces large salmon-colored flowers. The pollen parent, 'Royalty', produces red flowers. The new variety produces pink flowers.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—'Emily Post'.

*Pollen parent.*—'Royalty'.

Class: Grandiflora.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Flower

Blooming Habit: Recurrent.

A. Bud:

(1) *Size.*—Small.

(2) *Form.*—Pointed, tapered.

(3) *Color.*—When sepals first divide, bud color is near 54A.

(4) *Sepals.*—Longer than bud, about 2.5 cm to 3 cm long, spread and reflex when bloom opens; some sepals are foliaceous. Color: Near 144B on top surface, under surface is slightly lighter.

(5) *Peduncle.*—Length: About 6 cm to about 8.5 cm. Aspect: Small prickles. Strength: Erect, sturdy. Color: Near 144B.

(6) *Bracts.*—None observed.

B. Bloom:

(1) *Size.*—Average size when fully expanded — about 9 cm to about 10 cm.

(2) *Borne.*—Singly.

(3) *Form.*—Imbricated, petals ruffled at maturity, cup-shaped.

(4) *Petalage.*—Number of petals under normal conditions — about 22 to 24.

(5) *Color (⅓ to ½ open).*—Outer petals — Top surface: largest part of surface is near 39D with top edging of petal near 52C; Undersurface: near 56C. Inner petals — Top Surface: largely near 50D; very slight edging at top of petal of near 50B; Undersurface: near 56C. Base of petals — (Point of attachment): Near 1B. General tonality from a distance — Pink.

(6) *Color (fully open).*—Outer petals — Top surface: near 54D with edging of near 55B; Undersurface: near 55C with slight edging of near 55B. Inner petals — Top surface: near 52D; Undersurface: near 52D. Base of petals — (Point of attachment): Near 1B. General tonality from a distance — Pink.

(7) *Color change.*—As bloom ages: Lightens slightly. Petal top surface: Inner part of petal lightens which gives a slight effect of pink blend Petal undersurface — Inner part of petal lightens which gives a slight effect of pink blend. General tonality at a distance — Pink.

Petals:

(1) *Texture.*—Thick, smooth.

(2) *Appearance.*—Inside semi-velvety and outside matte.

(3) *Form.*—Oribcular with slightly ruffled edges.

(4) *Arrangement.*—Imbricated.
(5) *Petaloids.*—Few.
(6) *Fragrance.*—Strong musk.
(7) *Lasting quality.*—About 7–10 days and plant about 5 to 7 days as cut flower.
(8) *Persistence.*—Petals drop off cleanly.

Reproductive Organs

A. Stamens:
(1) *Arrangement.*—Regularly arranged around styles.
(2) *Stamens.*—Near 184B.
(3) *Anthers.*—Color near 20A.
(4) *Filaments.*—Near 154D with near 64A at top.
(5) *Pollen.*—Color — near 20A.
B. Pistils:
(1) *Styles.*—Bunched, uneven.
(2) *Stigmas.*—Color near 173D.
C. Characteristics of hips: Hips have not been observed.

Plant

A. Form: Upright.
B. Growth: Vigorous; about 50 cm to about 54 cm in height at first season.
C. Foliage: Compound 3 to 7 leaflets.
(1) *Size.*—Medium.
(2) *Quantity.*—Abundant.
(3) *Color.*—New foliage — upper side near 147A; underside near 141B; mature foliage — upper side near 147A, underside near 191A.
(4) *Shape.*—Ovate.
(5) *Texture.*—Upper side slightly leathery smooth; underside slightly leathery, smooth.
(6) *Edge.*—Serrated.
(7) *Serration.*—Denticulate.
(8) *Leaf stem.*—Color — medium green.
(9) *Stipules.*—Adnate and parallel.
(10) *Rachis.*—Small prickles on underside.
(11) *Petioles.*—Top near 147B, underside near 147C.
(12) *Auricle.*—Reflexing with middle enlarged, medium, slightly glandular, slender.
(13) *Resistance to disease.*—Very resistant to blackspot, mildew and rust.
D. Wood:
(1) *New wood.*—Color near 146C, bark smooth.
(2) *Old wood.*—Color near 146B, bark smooth.
E. Flower stem: About 30 cm to about 40 cm from last cut.
F. Thorns:
*Quantity.*—On main stalk, many; laterals from stalk, average.
*Form.*—Curved downward, wing-shaped.
*Length.*—Medium.
*Color.*—Near 146C.
*Position.*—Irregular.
*Prickles.*—Many.
G. Winter hardiness: Winter hardy in Watsonville, Calif.

I claim:

1. A new and distinct grandiflora rose plant variety, substantially as shown and described.

* * * * *

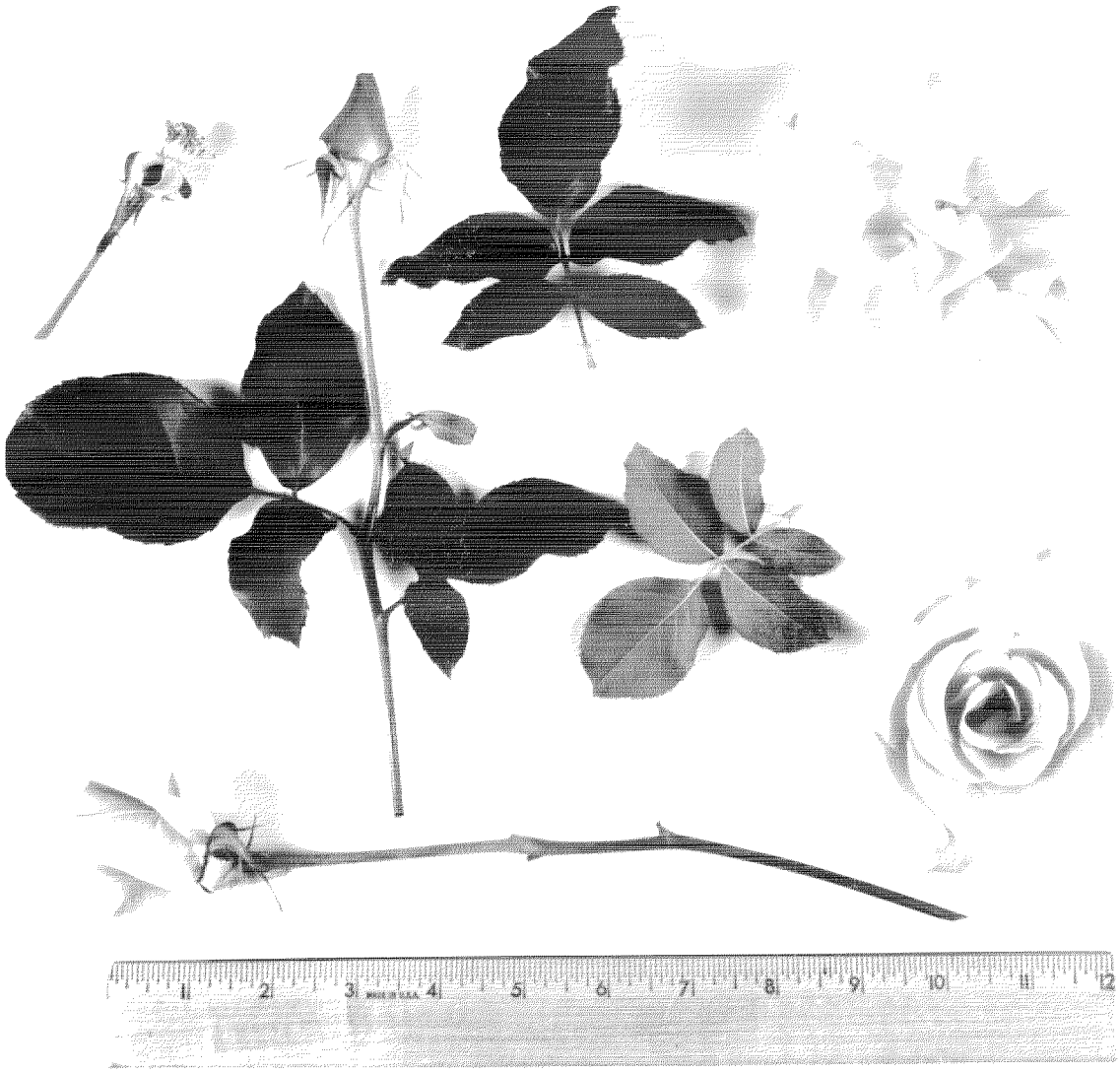
1
2
3
4
5
6
7
8
9
10
11
12

UNITED STATES PATENT AND TRADEMARK OFFICE

CERTIFICATE OF CORRECTION

PATENT NO. : Plant 10,155
DATED : December 23, 1997
INVENTOR(S) : Jerry Twomey

It is certified that error appears in the above-indentified patent and that said Letters Patent is hereby corrected as shown below:

Column 2, line 48, replace "Oribcular" with -- Orbicular --.
Column 3, line 4, replace "and" with -- on --.

Signed and Sealed this

Twenty-second Day of September, 1998

*Attest:*

Bruce Lehman

BRUCE LEHMAN

*Attesting Officer*

*Commissioner of Patents and Trademarks*